(12) United States Patent
Millau et al.

(10) Patent No.: US 8,785,118 B2
(45) Date of Patent: Jul. 22, 2014

(54) METHOD FOR FIXING A SUPERCOILED DNA AND THE USE FOR ANALYZING THE DNA REPAIR

(75) Inventors: Jean-François Millau, Grenoble (FR); Sylvie Sauvaigo, Grenoble (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 1522 days.

(21) Appl. No.: 11/922,572

(22) PCT Filed: Jun. 19, 2006

(86) PCT No.: PCT/FR2006/001378
§ 371 (c)(1),
(2), (4) Date: Feb. 2, 2009

(87) PCT Pub. No.: WO2006/136686
PCT Pub. Date: Dec. 28, 2006

(65) Prior Publication Data
US 2009/0176212 A1    Jul. 9, 2009

(30) Foreign Application Priority Data

Jun. 20, 2005  (FR) ..................... 05 06213

(51) Int. Cl.
*C12Q 1/68*     (2006.01)
*G01N 33/559*   (2006.01)
*A61K 9/14*     (2006.01)

(52) U.S. Cl.
CPC ...................... *C12Q 1/68* (2013.01)
USPC ............ 435/6.1; 435/333; 204/469; 424/487

(58) Field of Classification Search
USPC ................. 435/6.1, 433; 424/487; 204/469
See application file for complete search history.

(56) References Cited

U.S. PATENT DOCUMENTS

| 6,309,838 | B1 | 10/2001 | Chaubron et al. | |
|---|---|---|---|---|
| 2002/0022228 | A1 | 2/2002 | Nehls et al. | |
| 2003/0207265 | A1* | 11/2003 | Church | 435/6 |
| 2007/0020659 | A1* | 1/2007 | Zechiedrich et al. | 435/6 |

FOREIGN PATENT DOCUMENTS

| FR | 2 849 058 A1 | 12/2002 |
|---|---|---|
| WO | WO 99/49080 | 9/1999 |

OTHER PUBLICATIONS

Chiari et al, New type of large-pore polyacrylamide agarose mixed bed matrices for DNA electrophoresis: pore size estimation from Ferguson plots of DNA fragments, 1995, Electrophoresis, 16, 1337-1344.*
Akerman, Effects of Supercoiling in Electrophoretic Trapping of Circular DNA in Polyacrylamide Gels, 1998, Biophysical Journal, 74, 3140-3151.*
Garner et al, Resolution of circular, nicked circular and linear DNA, 4.4 kb in length, by electrophoresis in polyacrylamide solutions, Electrophoresis, 1992, 13, 176-178.*
English translation of the written opinion of the PCT/FR2006/001378, published Dec. 20, 2007, pp. 1-5.*
Kawamura et al., "A New Approach to the Detection of DNA Damage", Leukemia Research, vol. 13, No. 5, pp. 391-398, 1989.

* cited by examiner

*Primary Examiner* — Narayan Bhat
(74) *Attorney, Agent, or Firm* — William E. Beaumont

(57) ABSTRACT

A method for fixing a supercoiled DNA consists in depositing a supercoiled DNA sample on the surface of a porous polymer film, in fixing said supercoiled DNA therein by a passive diffusion, in obtaining a support by the inventive method and in using said support for analyzing the DNA distribution.

21 Claims, 2 Drawing Sheets

METHOD FOR FIXING A SUPERCOILED DNA AND THE USE FOR ANALYZING THE DNA REPAIR

The invention relates to a method for immobilizing supercoiled DNA and to the use of supercoiled DNA immobilized on a support, as substrate for analyzing the enzymatic reactions of DNA repair.

Biochips have become essential analytical tools for biomedical research and clinical diagnosis. These powerful tools make it possible to simultaneously analyze several tens of thousands to several hundred thousand samples by means of DNA probes (oligonucleotides, cDNA, PCR amplification products) or protein probes (antibodies, peptides), immobilized on a support.

Biochips are prepared using a support (glass, polypropylene, polystyrene, silicone, metal, nitrocellulose or nylon), optionally modified with a porous film [glass coated with nylon (Atlas Arrays™; Clontech); silicone coated with a hydrogel (Nanochip™; Nanogen), glass coated with a gel of acrylamide polymer, Hydrogel™ (Perkin-Elmer) or of methacrylate polymer (U.S. application 2005/0042363)].

Two types of methods are used to immobilize the DNA probe or protein probe to the support:

Deposition of Presynthesized Probes and Immobilization by Covalent or Noncovalent Coupling The probe (oligonucleotide (10 to 25 bases), peptide, cDNA or PCR amplification fragment (maximum of 500 bp to 0.2 kb), protein (antibody)) is generally deposited onto the support by means of an automatic distributor (Lemmo et al., Current Opinion in Biotechnology, 1998, 9:615-617). The probe, which is charged, can also be deposited at the surface of a support based on micro-electrodes coated with a permeable layer (agarose gel), and transported into the gel by electrophoresis (Heller et al., Electrophoresis, 2000, 21:157-164).

In addition, in the specific case of the colony-hybridization technique (Hanahan and Meselson, Gene, 1983, 10:63-67), colonies of bacteria deposited on a support are transferred onto a nylon or nitrocellulose filter and then lyzed so as to release the DNA (plasmid or cosmid) on the filter.

The probe is then immobilized on the support by means of covalent or noncovalent (hydrophobic, electrostatic) bonds or of a combination of the two.

Covalent bonds are generally formed between the reactive functional groups of an activated support and those of a probe modified at one of its ends (phosphate or carboxylic acid group for the probe and amine for the support, and vice versa; amine group for the probe and isothiocyanate, aldehyde or epoxy for the support; Zammateo et al., Analytical Biochemistry, 2000, 208:143-150).

When the support is coated with a polyacrylamide film, it may be activated by substitution of hydrazide groups by treatment with hydrazine. Probes 3'-modified with a 3-methyluridine group are oxidized in the presence of periodate so as to form a reactive aldehyde, and are then deposited on the support. The reaction of the aldehyde groups of the probe with the hydrazine groups of the gel forms covalent bonds which immobilize the DNA in the acrylamide gel (Khrapko et al., DNA sequence, 1991, 6:375-388; Yershov et al., P.N.A.S., 1996, 93:4913-4918). It is also possible to immobilize aminated DNA fragments, less than 500 nucleotides in length, during the polymerization of the gel (Rubina et al., Anal. Biochem., 2004, 325:92-106).

The supports coated with hydrogel make it possible in particular to increase the immobilization capacity of the support and to improve the probe's environment, the sensitivity and the detection threshold.

In addition, UV-irradiation or homofunctional or bifunctional coupling agents can also form covalent bonds between the amine groups of a support coated with poly-L-lysine, and either the thymidine residues of DNA (UV) or the amine groups of a modified probe (glutaraldehyde).

Noncovalent bonds comprise mainly electrostatic interactions between the DNA and a support coated with poly-L-lysine.

Synthesis and Immobilization of Probes In situ

This method, which can be used only for the preparation of oligonucleotide chips (Southern et al., Genomics, 1992, 4, 1008-1017) or peptide chips, makes it possible to simultaneously carry out the covalent coupling and the synthesis of the oligonucleotides on an area which is delimited, in particular using a mask (mechanical or photolithographic mask).

These methods make it possible to obtain biochips suitable for many applications: genetic analysis (sequencing, mapping, polymorphism, mutations, gene copy number, expression profile) and analysis of protein/ligand interactions (immunoassays; interactions between proteins and DNA molecules or RNA molecules or small molecules).

However, certain analyses, such as that of DNA repair activity, use a specific DNA probe, i.e. a supercoiled circular double-stranded DNA (supercoiled plasmid), the structure of which must imperatively be preserved during the immobilization of the DNA to the support, and conserved once the DNA has been immobilized to the support. In fact, the substrate used for analyzing DNA repair is a supercoiled plasmid with damaged purine or pyrimidine bases (oxidative, photoinduced, chemical adduct damage), damaged sugars, damage to the structure of the double helix (inter- or intra-strand bridging, intercalated agents), and/or breaks, induced by treatment of the plasmid with various genotoxic agents, and then purification of the supercoiled plasmid on a sucrose or cesium gradient. The purification of the supercoiled plasmid makes it possible to eliminate plasmids comprising breaks (relaxed structure). This is because, unlike the other types of damage mentioned above, which preserve the supercoiled structure of the DNA, breaks destroy the supercoiled structure of the plasmid and form a relaxed structure. The non-treated supercoiled plasmid (plasmid without damage) serves as a control. The biological sample to be analyzed is incubated in the presence of the supercoiled plasmid comprising damage (damaged plasmid) and of a labeled nucleoside triphosphate. The DNA repair activity is subsequently quantified by measuring the amount of label incorporated into the damaged plasmid, in comparison with the control plasmid.

The undirected damage to the DNA, and in particular the breaks (single-stranded or double-stranded) that have appeared during the immobilization of the plasmid to a support and subsequently during the conservation of the plasmid immobilized to a support, is repaired by the repair systems contained in the samples to be analyzed. Thus, the presence of breaks, in addition to the modified bases, leads to the incorporation of parasitic labels which are quantified and mask the specific base-repair response. Furthermore, the breaks induce relaxation of the plasmid and thus allow easier access to the nucleases of the biological medium, leading to an increase in the plasmid repair activity. Finally, the relaxed structures promote the initiation of undesired polymerization reactions. The repair of undirected damage to the DNA and, in particular, of breaks can thus mask or interfere with the repair of specific damage. The specific signal of the damage studied may thus be lost in the background noise generated by the nonspecific signals, making it difficult, or even impossible, to analyze the DNA repair.

Most of the methods for preparing biochips do not make it possible to immobilize DNA that is large in size and has a specific structure, such as plasmids (supercoiled circular DNA), while preserving their integrity.

In fact, the immobilization of supercoiled DNA by noncovalent coupling on slides coated with poly-L-lysine as described in patent application FR 02 16435 does not make it possible to preserve the DNA structure in a stable manner, and the supports comprising the immobilized plasmid must be used immediately after immobilization of the DNA, thereby limiting their industrial use. The interactions between the DNA, the internucleoside phosphate groups of which are negatively charged, and the cationic groups of the poly-L-lysine produce more or less rapidly an instability in the supercoiled structure of the plasmid, resulting in the appearance of breaks in the DNA and in the priming of undesired repair reactions. Consequently, an increase in the repair rate of the nonmodified plasmid serving as a control is observed a few hours after deposition on the poly-L-lysine slides, compared with a reaction carried out immediately after deposition. This repair rate detected on the control plasmid increases proportionally to the conservation time of the slides. The same phenomenon occurs on plasmids comprising damage to the DNA and masks the expected specific response. Thus, the slides must be used very rapidly after deposition of the plasmids, which is a major disadvantage for industrial use.

The conservation of the poly-L-lysine slides on which plasmids are immobilized is, moreover, very dependent on the hygrometric environment during the deposition of the plasmids and the storage of the slides. However, this parameter is difficult to control precisely, which results in random conservation times for the slides. The random nature of the conservation further limits the use of this technique. In addition, even though the deposition of the plasmid can optionally be carried out in a humid atmosphere, this alternative is not satisfactory since the attachment of the plasmid to the poly-L-lysine slide is less effective and the repair signals obtained are weak.

Another disadvantage of this method is related to the volume of the deposits of plasmid solutions on the slide. It is of the order of a few hundred picoliters; however, since the rate of evaporation of the water contained in the deposits is dependent on factors such as the ambient humidity, the ambient temperature and the adjuvants possibly present in the depositing solution, there is always a risk that rapid evaporation of the water will lead to concentration of the sample at the circumference of the drop and therefore to a lack of homogeneity of the deposit. The lack of homogeneity of the deposit results in difficulties when quantifying the repair signal at the level of the deposit, and yet a precise quantification is necessary for determining the repair capacities of a given cell medium and for comparing various media with one another. Rickman et al. (Nucleic Acids Res., 2003, 31, e109) have, nevertheless, shown that certain adjuvants slow down the evaporation. However, the use of such compounds leads to a morphological heterogeneity or an increase in size of the deposits. Certain compounds appear to give advantageous results in terms of quality of deposition, but are not suitable for repair studies since they can cause denaturation of the plasmid, as is the case with formamide (Rickman et al., 2003, mentioned above).

Covalent coupling of the DNA to the support cannot be envisioned since it generates stresses that result in the appearance of breaks on the plasmid. In addition, it involves chemical and/or physical treatment steps (heating, UV-irradiation) that may introduce damage into the DNA. In addition, in situ synthesis methods can be used only for the preparation of oligonucleotide chips.

Consequently, there exists a real need to provide alternative methods for immobilizing supercoiled DNA on a support, which more satisfactorily meet the needs in the field in that they observe the integrity of the supercoiled structure of the DNA and that they make it possible to conserve this structure for the purpose of subsequent use of the DNA, in particular as a substrate in enzymatic DNA repair reactions.

The inventors have shown that supercoiled DNA can be stably immobilized in a porous polymer film, by passive diffusion of the DNA not activated with reactive functional groups (nonfunctionalized), in a polymer film, also not activated. Under these conditions, the DNA immobilized conserves its supercoiled structure for several months, even when it comprises damage introduced by exposure to genotoxic agents. The DNA is advantageously immobilized on a miniaturized support coated with a porous polymer film, which allows the preparation of large amounts of samples of immobilized DNA, and the storage thereof for the purpose of subsequent use in particular as a substrate in DNA repair reactions.

Consequently, a subject of the present invention is a method for immobilizing a supercoiled DNA, characterized in that it comprises the following steps:
depositing a supercoiled DNA sample on the surface of a porous polymer film, and
immobilizing the supercoiled DNA by passive diffusion in said porous polymer film.

DEFINITIONS

Supercoiled DNA: a supercoiled circular double-stranded DNA molecule, in particular a plasmid.
Porous polymer film: a thin layer of a three-dimensional matrix comprising chains of one or more polymers and a solvent, which matrix includes interstices (pores) that can contain macromolecules such as DNA. The thickness of the polymer film is sufficiently small to limit the background noise. The thickness of the film is preferably less than 0.1 mm.
immobilization: the penetration of the DNA by passive diffusion within the three-dimensional matrix consisting of chains of one or more polymer(s) and of a solvent.

Under these conditions, the supercoiled DNA, diluted in a conventional buffer known to those skilled in the art, in particular PBS, pH 7.4, penetrates the porous polymer film in the absence of electric current (no electrophoresis step) and is immobilized in the interstices of the polymer matrix, in the absence of any subsequent physical or chemical treatment of the polymer film or of the DNA. The supercoiled DNA thus immobilized is stably maintained in the polymer film for several months.

Among preferred porous polymers, mention may be made of extendable aqueous polymers (hydrogel or aqueous gel: polysaccharide, and particularly agarose) and polymers in which covalent chemical bonds are established between the polymer chains, so as to form a mesh (polyacrylamide).

The amount of DNA immobilized in the polymer (immobilization capacity) depends on the nature of the polymer and on its concentration and can be increased by adding a DNA adsorbent to the hydrogel.

According to a first advantageous embodiment of said method, the polymer film is a polyacrylamide hydrogel. It preferably comprises 5% to 15% of a 50:1 to 5:1 acrylamide:methylenebisacrylamide mixture, preferably 5% to 15% of a 19:1 mixture.

According to a second advantageous embodiment of said method, the polymer film comprises 0.1% to 5% of a DNA adsorbent such as gelatin, collagen or a polysaccharide, for instance agarose, dextran or a glucose or sucrose polymer, or else a mixture of said adsorbents. Said adsorbent is preferably agarose, preferably a low-melting-point agarose, the melting temperature of which is advantageously below 40° C.

According to an advantageous arrangement of the above embodiments, the polymer film is a polyacrylamide hydrogel comprising 10% of a 19:1 acrylamide:methylenebisacrylamide mixture and 0.8% of low-melting-point agarose.

According to a third advantageous embodiment of said method, said supercoiled DNA is a plasmid.

According to a fourth advantageous embodiment of said method, said supercoiled DNA contains damage induced by a genotoxic agent. Preferably, said damage was induced by treatment of an isolated plasmid or of cells comprising said plasmid, with a physical or chemical genotoxic agent. Among this damage, mention may be made of damage to the purine or pyrimidine bases (oxidative, photo-induced, chemical adduct damage), damage to the sugars, damage to the structure of the double helix (inter- or intra-strand bridging, intercalated agents) and breaks.

According to a fifth advantageous embodiment of said method, the porous polymer film is deposited onto an appropriate support known to those skilled in the art, such as a glass, metal, silicone or plastic support. It is preferably a miniaturized support of the microchip type. It is preferably a glass slide.

A subject of the present invention is also a support coated with a porous polymer film, comprising a immobilized supercoiled DNA, which may be obtained by means of the immobilization method as defined above.

It is advantageously a glass slide coated with a polyacrylamide hydrogel comprising a damaged supercoiled DNA.

The polymerization and the deposition of the polymer film at the surface of a support are carried out according to the conventional techniques known to those skilled in the art. All the known techniques can be used for implementing the invention. A porous polymer such as a polyacrylamide hydrogel is prepared from an aqueous solution containing acrylamide and polymerization means. For example, (i) 5% to 15% of an acrylamide:methylenebisacrylamide mixture (50:1 to 5:1, preferably 19:1), (ii) 0% to 5% of DNA adsorbent(s) as defined above, preferably a polysaccharide, and particularly low-melting-point agarose, and (iii) a source of radicals, for example 0.001% to 0.1% of ammonium persulfate together with 0.001% to 0.5% of TEMED (N,N,N',N'-tetramethylethylenediamine).

Ready-prepared polymer compositions can also be used, in particular hydrogels such as HydroGel™ (Perkin-Elmer; www.perkinelmer.com/proteomics).

The support is, for example, a glass slide precoated with aminosilane. The aqueous solution of hydrogel is subsequently deposited on and spread over the support, using suitable means such as a glass coverslip, so as to form a thin homogeneous layer. The hydrogel is polymerized, optionally by heating or exposure to ultraviolet rays, depending on the polymerization means used. The support coated with a polymer film thus obtained can optionally be dried, preferably by heating.

The DNA, in particular a plasmid, is prepared according to the conventional molecular biology techniques, using the standard protocols as described in *Current Protocols in Molecular Biology* (Frederick M. Ausubel, 2000, Wiley and Son Inc., Library of Congress, USA).

The treatment of the DNA with genotoxic agents is carried out according to the conventional techniques known to those skilled in the art, according to the standard protocols as described in patent application FR 0216435.

The supercoiled DNA fraction is isolated by sucrose gradient and/or cesium chloride gradient centrifugation, according to the standard protocols as described in patent application FR 0216435.

The supercoiled DNA is diluted to a concentration of preferably between 5 and 100 µg/ml, and advantageously from 20 to 40 µg/ml, in a standard buffer such as PBS, pH 7.4.

The supercoiled DNA is then deposited onto the areas of the support that are coated with hydrogel, for example using a robot such as a piezoelectric robot.

A subject of the present invention is also the use of an aqueous composition comprising 10% of a 19:1 acrylamide:methylenebisacrylamide mixture and 0.8% of low-melting-point agarose, for immobilizing supercoiled DNA.

A subject of the present invention is also the use of a supercoiled DNA immobilized in a porous polymer film as defined above, as substrate for analyzing DNA repair in a biological medium.

The DNA repair can in particular be analyzed according to the method for the quantitative evaluation of overall and specific capacities for DNA repair described in application FR 0216435.

The analysis of DNA repair in a biological medium, and in particular the quantitative evaluation of the overall and specific capacities for DNA repair in a biological medium, makes it possible in particular to establish the repair profile of a given medium, to diagnose a DNA repair-related disease, to evaluate the influence of a physical or chemical treatment on the repair capacities of a given biological medium, and to screen for substances capable of modulating the repair system of a biological medium.

The use of hydrogel instead of poly-L-lysine, for immobilizing the supercoiled DNA (DNA comprising damage (damaged supercoiled plasmid) and controlled DNA (supercoiled plasmid)), has the following advantages, in particular for measuring the DNA repair activity in a biological medium:

Stability of the Plasmid Immobilized in the Hydrogel:

The plasmid immobilized on a hydrogel-coated support, for example an acrylamide polymer, conserves its supercoiled structure despite the damage to the DNA, for several weeks, in an environment that is uncontrolled from the point of view of hygrometry. Thus, large amounts of slides comprising the immobilized plasmid can be simultaneously prepared and readily stored until they are used several weeks later.

DNA Repair Detection Sensitivity

The range of values of the repair signal is broader, which allows a more accurate analysis of the samples whose repair activity is analyzed, and in particular better discrimination with respect to the differences between the samples analyzed.

BRIEF DESCRIPTION OF DRAWINGS

In addition to the above arrangements, the invention also comprises other arrangements which will emerge from the following description, which refers to examples of use of damaged supercoiled DNA, immobilized in a hydrogel, as substrate for an enzymatic DNA repair reaction, and also to the attached drawings in which.

Figure 1:
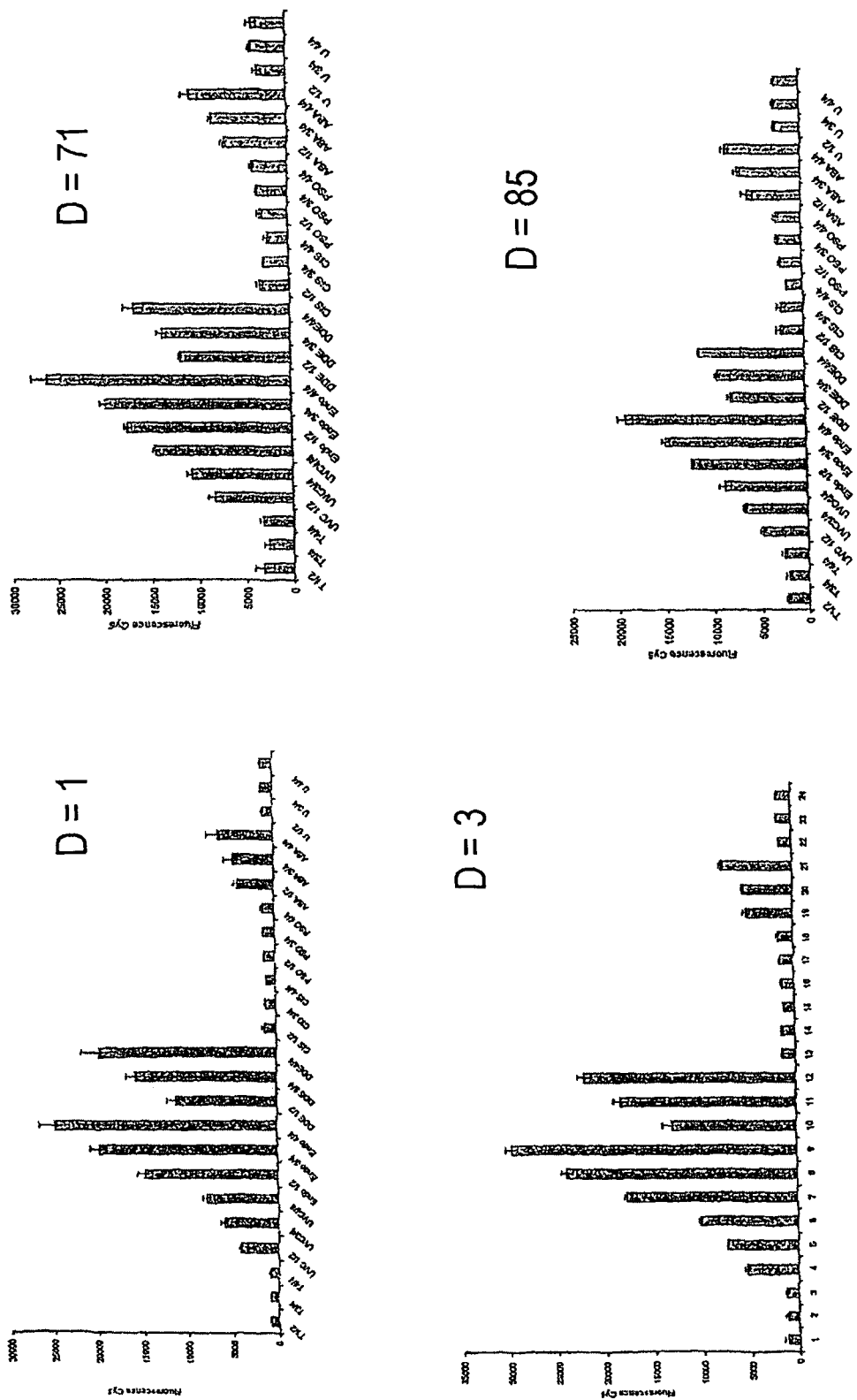
FIG. 1 illustrates the stability at +4° C., for a period of 85 days, of a damaged supercoiled DNA, immobilized on glass slides coated with a polyacrylamide hydrogel. Supercoiled plasmid DNA exhibiting damage induced by various physical or chemical agents was prepared as described in example 1, and then diluted using control (nontreated) plasmid so as to keep the total concentration of plasmid in the PBS buffer at 40 µg/ml: damaged plasmid only (4/4); 30 µg/ml of damaged plasmid and 10 µg/ml of control plasmid (3/4); 20 µg/ml of damaged plasmid and 20 µg/ml of control plasmid (1/2). Nontreated plasmid DNA was used as control. The DNA samples were deposited onto glass slides coated with a polyacrylamide hydrogel and the slides were then conserved at +4° C. for 1, 3, 71 and 85 days ($D_1$, $D_3$, $D_{71}$, and $D_{85}$) before evaluating the DNA repair by measuring the emission of fluorescence. The fluorescence values are expressed in arbitrary units (a.u.). T: control. UVC: UVC-irradiation (0.3 $J/cm^2$). endo: treatment with naphthalene endoperoxide. DDE: treatment with trans,trans-2,4-decadienal. CIS: treatment with cisplatin. PSO: treatment with psoralene. ABA: induction of abasic sites. U: introduction of uracil.

It should be understood, however, that these examples are given only by way of illustration of the subject of the invention, of which they no way constitute a limitation.

EXAMPLE

Use of a DNA Immobilized in a Hydrogel as Substrate for Analyzing DNA Repair The principle of the DNA repair test which was used to compare the repair of DNA immobilized on a support coated either with poly-L-lysine or with hydrogel, is described in patent application FR 0216435.

1) Materials and Methods
a) Preparation of Supercoiled DNA Comprising Damage

The plasmid (pBluescript II, Stratagene) is produced by transformation of the XL1 blue MRF' strain of *E. coli* (Stratagene) according to the protocol supplied by the supplier. The plasmid is purified using the Plasmid midi Kit™ (Qiagen) and diluted in PBS buffer (10 mM phosphate, pH 7.4, 137 mM NaCl, 2 mM KCl).

The plasmid is treated with various physical or chemical agents in order to introduce damage therein, i.e.:

UVC-Irradiation (UVC)

The plasmid in solution in PBS (25 µl; 40 µg/ml) is irradiated with a lamp emitting at 254 nm. The received dose is 0.3 $J/cm^2$ (FIGS. 1 and 2) or alternatively 0.03, 0.06 and 0.12 $J/cm^2$ (FIG. 3).

Treatment with Naphthalene Endoperoxide (Endo)

20 µl of naphthalene endoperoxide at 50 mM (N,N'-di-(2,3-dihydroxypropyl)-1,4-naphthalenedipropanamide 1,4-endoperoxide, prepared according to the protocol described in J. Biol. Chem., 2000, 275, 40601-40604) are incubated with 200 µl of plasmid at 1 mg/ml in PBS, for 2 hours at 37° C.

Treatment with Trans,Trans-2,4-Decadienal (DDE)

200 µl of plasmid at 1 mg/ml in PBS are mixed with 200 µl of 0.2 M carbonate/bicarbonate buffer, pH 9.2, and 200 µl of tetrahydrofuran, to which 4 µl of DDE (5.7 M) and 12 µl of $H_2O_2$ (8.8 M) are added. The mixture is incubated at 50° C. for 16 hours in the dark. The DDE is then removed by two extractions with dichloromethane.

Treatment with Cisplatin (CIS)

150 µl of plasmid at 1 mg/ml in PBS are treated with 1 µl of a solution of cis-diamine dichloroplatinum (II) at 15 mg/ml in dimethyl sulfoxide (DMSO), for 2 hours at 37° C.

Treatment with Psoralene (PSO)

150 µl of plasmid at 1 mg/ml in PBS are mixed with 20 µl of a solution of psoralene amine at 120 µM, and irradiated at 365 nm at a dose of 1.48 $J/cm^2$.

Creation of Abasic Sites (ABA)

100 µl of plasmid at 1 mg/ml are incubated in sodium citrate at 0.05 M, pH 4.8, containing 12 µl of KCl (2 M), for 4 hours at 70° C.

Introduction of Uracil (U)

The plasmid (pBluescript II, Stratagene) is produced by transformation of an *E. coli* strain deficient for uracil-DNA-glycosylase activity ($UNG^-$), according to the protocol supplied by the supplier. The plasmid is purified using the Plasmid midi Kit™ (Qiagen) and then on a sucrose gradient.

The treated plasmid is then precipitated and purified on a sucrose gradient, and the fractions containing at least 90% of supercoiled plasmid are harvested, as described in application FR 0216435. The various preparations of supercoiled DNA containing damage, and also the nontreated control plasmid comprising supercoiled DNA with no damage, are diluted to 40 µg/ml in PBS.

b) Preparation of the Supports and Deposition of DNA

The glass slides coated with poly-L-lysine are provided by VWR International.

$b_1$) Preparation of Glass Slides Coated with a Polyacrylamide Hydrogel

Glass slides (76×26 mm) are placed in a slide holder, and then incubated in a solution comprising 4 ml of Bind-Silane (3-methacryloxypropyltrimethoxysilane) and 220 µl of glacial acetic acid in a total volume of one liter of distilled water, for 1 hour, with agitation. The slides are then rinsed three times with distilled water and once with ethanol, and then dried in a suction hood.

The polyacrylamide hydrogel is an aqueous solution, that can also be prepared from a PBS buffer (or from a TBE buffer), containing: 10% of a 19:1 mixture of acrylamide and methylenebisacrylamide, 0.8% of low-melting-point agarose (Tebu-Bio), 0.06% of ammonium persulfate and 0.065% of TEMED (N,N,N',N'-tetramethylethylenediamine). 100 µl of this solution are deposited uniformly onto a glass slide (76×26 mm), prepared as above, and then spread thinly and evenly using a glass coverslip. The slide covered with the coverslip is heated at 40° C. for 5 minutes, so as to allow the gel to set. The glass coverslip is then removed, and the slide bearing the gel is then again heated at 40° C., for 3 minutes, in order to dry the hydrogel. The polyacrylamide hydrogel-coated slides are conserved at +4° C. They are preferably conserved for at least 24 h at +4° C. before being used.

b₂) Deposition of DNA Samples

Figure 2:
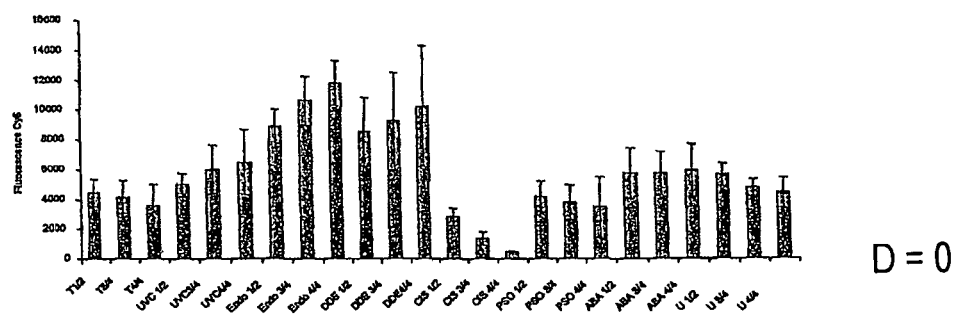
FIG. 2 illustrates the stability at +4° C. of a damaged supercoiled DNA, immobilized on glass slides coated with poly-L-lysine. Supercoiled plasmid DNA exhibiting damage induced by various physical or chemical agents was prepared as described in example 1, and then diluted using control (nontreated) plasmid so as to keep the total concentration of plasmid in the PBS buffer at 40 µg/ml: damaged plasmid only (4/4); 30 µg/ml of damaged plasmid and 10 µg/ml of control plasmid (3/4); 20 µg/ml of damaged plasmid and 20 µg/ml of control plasmid (1/2). Nontreated plasmid DNA was used as control. The DNA samples were deposited onto glass slides coated with poly-L-lysine and then the DNA repair was evaluated immediately after deposition by measuring the emission of fluorescence ($D_0$) or the slides were conserved at +4° C. for 1 day ($D_1$) before evaluating the DNA repair. T: control. UVC: UVC-irradiation (0.3 $J/cm^2$). endo: treatment with naphthalene endoperoxide. DDE: treatment with trans,trans-2,4-decadienal. CIS: treatment with cisplatin. PSO: treatment with psoralene. ABA: induction of abasic sites. U: introduction of uracil.
Figure 2:
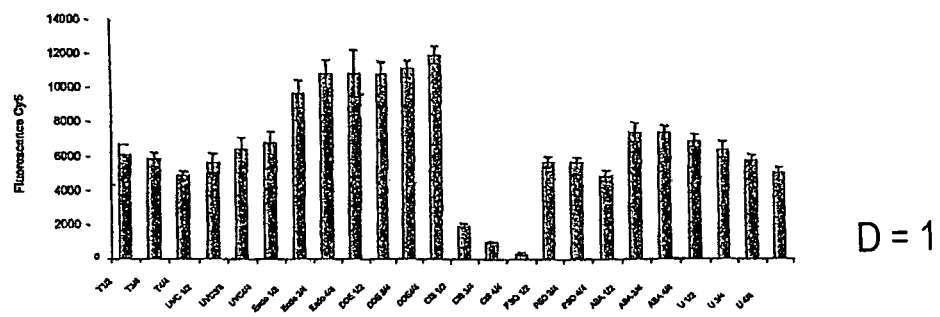

The total plasmid concentration in the samples is 40 µg/ml in the PBS buffer, and more specifically with reference to FIGS. 1 and 2: damaged plasmid alone (4/4); 30 µg/ml of damaged plasmid and 10 µg/ml of control plasmid (3/4); 20 µg/ml of damaged plasmid and 20 µg/ml of control plasmid (1/2). The undamaged supercoiled plasmid DNA is used as control.

Three drops of DNA sample (total volume of approximately 500 picoliters) are deposited onto each area of the slide, using a piezoelectric robot (Scieflexarrayer, Scienion).

The poly-L-lysine-coated slides are used immediately after deposition ($D_0$) or are conserved for 24 h at 4° C. ($D_1$) before analyzing the DNA repair ($D_1$).

After passive immobilization of the DNA, at 4° C. for 24 h, the hydrogel-coated slides are used for analyzing the DNA repair ($D_1$), or conserved at the same temperature for a varying period of time, before analyzing the DNA repair ($D_3$, $D_{71}$, $D_{85}$).

c) Repair Reaction and Measurement of the Repair Signal

A solution (30 µl) containing a cell lysate liable to contain DNA repair systems (25 µl; 0.6 mg/ml of proteins of nuclear extracts from HeLa cells; Cil Biotech) and various compounds required in order for the proteins of the biological medium to carry out the repair reaction (5 µl of ATG buffer (200 mM Hepes KOH pH 7.8, 356 mM MgCl₂, 2.5 mM DTT, 1.25 pM dATP, 1.25 pM dGTP, 1.25 pM TTP, 17% glycerol, 10 mM EDTA, 250 µg/ml creatine phosphokinase, 50 mM phosphocreatine, 10 mM ATP, 1.25 µM dCTP-Cy5)) is deposited onto each area of the slide containing the various samples of immobilized DNA. The slides are incubated for 3 hours at 30° C. The slides are then washed successively in PBS containing 0.5% of Tween 20 (2 washes of 3 min) and in distilled water (2 washes of 3 min). After drying by centrifugation (800 rpm, 3 min), the fluorescent signal is measured (Genepix 4200A scanner, Axon) and analyzed using the Genepix Pro 5.1 software (Axon). The signals are normalized relative to the median of the signals of each area.

2) Results a) Improvement in the Sensitivity of the DNA Repair Evaluation

The DNA immobilized on a hydrogel-coated slide makes it possible to increase the sensitivity of detection of the DNA repair activity, as shown by the comparison of the DNA repair measurements carried out after passive immobilization of the DNA samples (FIG. 1).

In fact, in comparison with the use of poly-L-lysine (signals of between 9000 and 12 000 arbitrary units for the various damage at $D_0$), the use of the polyacrylamide hydrogel makes it possible to obtain DNA repair signals within a larger range of values (signals of between 11 000 and 20 000 arbitrary units for the various damage at $D_1$), irrespective of the type of DNA damage for which the repair is studied. This difference could be explained by an improvement in the amount and/or in the quality of the DNA immobilized in the hydrogel and in the efficiency of the repair reaction in this medium.

b) Stability of the Immobilized DNA

The DNA immobilized on the hydrogel-coated slide is stable for more than 2 months, as shown by the results of the DNA repair tests carried out at various times after deposition of the DNA on the hydrogel (FIG. 1). At $D_{71}$, the DNA repair activity is comparable to that detected at $D_1$, irrespective of the type of damage for which the repair is studied. In addition, the lower background noise observed at $D_1$ with the control DNA reflects a better preservation of the structure of the DNA during the immobilization of the DNA in the hydrogel.

By comparison, with the DNA immobilized on a poly-L-lysine-coated slide, a higher background noise is observed at $D_0$ with the control DNA, as is a rapid increase in the DNA repair signal ($D_1$), both in the control DNA samples and the damaged DNA, indicating the appearance of additional breaks in the DNA.

The invention claimed is:

1. A method for immobilizing a supercoiled DNA, which comprises the steps of:
   a) depositing the supercoiled DNA sample on a surface of a porous polymer film, and b) immobilizing the supercoiled DNA by a passive diffusion in said porous polymer film, wherein the immobilization of the supercoiled DNA comprises no additional electrophoretic or physical or chemical treatment of the porous polymer film or the supercoiled DNA.

2. The method of claim 1, wherein the porous polymer is a polyacrylamide hydrogel.

3. The method of claim 2, wherein the polyacrylamide hydrogel comprises 5% to 15% of a 50:1 to 5:1 acrylamide: methylenebisacrylamide mixture.

4. The method of claim 3, wherein the polyacrylamide hydrogel comprises 5% to 15% of a 19:1 acrylamide:methylenebisacrylamide mixture.

5. The method of claim 1, wherein the polymer film comprises 0.1% to 5% of DNA adsorbent(s).

6. The method of claim 1, wherein the adsorbent is a polysaccharide.

7. The method of claim 6, wherein the adsorbent is agarose.

8. The method of claim 7, wherein the adsorbent is low-melting-point agarose.

9. The method of claim 8, wherein the low-melting-point agarose has a melting temperature of below 40° C.

10. The method of claim 4, wherein the polyacrylamide hydrogel comprises 10% of a 19:1 acrylamide:methylenebisacrylamide mixture and 0.8% of low-melting-point agarose.

11. The method of claim 1, wherein said supercoiled DNA is a plasmid.

12. The method of claim 1, wherein said supercoiled DNA of step a) contains damaged induced by a genotoxic agent.

13. The method of claim 1, wherein the porous polymer film is deposited onto a support.

14. The method of claim 12, wherein said support is a glass slide.

15. The method of claim 1, wherein the supercoiled DNA sample is deposited on the surface of the porous polymer film by a piezoelectric robot.

16. A support coated with a porous polymer film, comprising an immobilized supercoiled DNA, which is produced by the method of claim 1.

17. The support of claim 16, which is a glass slide coated with a polyacrylamide hydrogel comprising a damaged supercoiled DNA.

18. The support of claim 16, which is produced by depositing the porous polymer film onto a support.

19. The support of claim 18, wherein the support is a glass slide.

20. The support of claim 18, which is coated with a polyacrylamide hydrogel comprising the supercoiled DNA of step a), which is damaged.

21. A method of analyzing an enzymatic reaction of DNA repair, which which comprises the step of conducting an enzymatic DNA repair reaction, wherein an immobilized supercoiled DNA is used as a substrate for said enzymatic reaction; and wherein the immobilized supercoiled DNA is produced by the method of claim 1.

* * * * *